US008749783B2

(12) United States Patent
Wood et al.

(10) Patent No.: US 8,749,783 B2
(45) Date of Patent: Jun. 10, 2014

(54) SYSTEM AND METHOD FOR ANALYZING PORE SIZES OF SUBSTRATES (75) Inventors: Stewart P. Wood, Midland, MI (US); Charles F. Broomall, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/817,016

(22) PCT Filed: Sep. 26, 2011

(86) PCT No.: PCT/US2011/053226
§ 371 (c)(1),
(2), (4) Date: Feb. 14, 2013

(87) PCT Pub. No.: WO2012/044570
PCT Pub. Date: Apr. 5, 2012

(65) Prior Publication Data
US 2013/0141722 A1 Jun. 6, 2013

Related U.S. Application Data (60) Provisional application No. 61/388,645, filed on Oct. 1, 2010.

(51) Int. Cl.
*G01N 21/00* (2006.01)
*G01N 21/53* (2006.01)
*G01N 21/954* (2006.01)

(52) U.S. Cl.
CPC .............. *G01N 21/53* (2013.01); *G01N 21/954* (2013.01)
USPC ....................... 356/338; 356/241.1; 356/241.5

(58) Field of Classification Search
CPC ..................................................... G01N 21/53
USPC ............................ 356/334–342, 241.1–241.5
See application file for complete search history.

(56) References Cited

U.S. PATENT DOCUMENTS 3,351,760 A 11/1967 Brown
5,076,692 A 12/1991 Neukermans et al.
(Continued)

FOREIGN PATENT DOCUMENTS

EP 0 445 962 A2 11/1991
EP 1 607 734 A1 12/2005
(Continued)

OTHER PUBLICATIONS

International Search Report and Written Opinion for corresponding PCT Application No. US2011/053226 filed Sep. 26, 2011; dated Jan. 24, 2012.
(Continued)

*Primary Examiner* — Michael P Stafira (57) ABSTRACT

A system for analyzing the pore size of a substrate or device containing substrates adapted to separate fluids and has at least two surfaces, a first and a second surface, which are isolated from, one another and wherein the substrate or devices containing the substrates have an exit for fluids passing through the substrate, comprising: a) a particle generator (15) capable of generating particles of a controlled size; b) a system (18) for creating a pressure differential between the first and the second surface of the substrate; c) a light source (24) spaced front the exit of the substrate or device containing the substrate adapted for illuminating particles exiting the exit of the substrate or device containing the substrate; d) a closed flow path from the particle generator to the first surface of the substrate; e) a substrate or device holder (11) adapted for holding the substrate or device in the proper location in the system; and f) one or more reference images. Also described are methods of utilizing the system to identify pore sizes of substrates.

18 Claims, 2 Drawing Sheets

(56) References Cited

U.S. PATENT DOCUMENTS

| | | | |
|---|---|---|---|
| 5,102,434 | A | 4/1992 | Hijikata et al. |
| 5,424,536 | A | 6/1995 | Moriya |
| 5,463,462 | A | 10/1995 | Muto et al. |
| 5,471,298 | A | 11/1995 | Moriya |
| 5,581,017 | A | 12/1996 | Bejtlich |
| 5,790,247 | A | 8/1998 | Henley et al. |
| 6,266,137 | B1 | 7/2001 | Morinaga |
| 6,452,670 | B1 | 9/2002 | Bour et al. |
| 6,496,258 | B1 | 12/2002 | Leipertz et al. |
| 6,630,996 | B2 | 10/2003 | Rao et al. |
| 6,666,070 | B1 | 12/2003 | Hagg et al. |
| 6,731,384 | B2 | 5/2004 | Oshima et al. |
| 6,797,975 | B2 | 9/2004 | Nishiyama et al. |
| 6,803,015 | B2 | 10/2004 | Vance et al. |
| 6,809,809 | B2 | 10/2004 | Kinney et al. |
| 6,936,835 | B2 | 8/2005 | Nishiyama et al. |
| 6,998,630 | B2 | 2/2006 | Nishiyama et al. |
| 7,012,678 | B2 | 3/2006 | Enomoto et al. |
| 7,012,685 | B1 | 3/2006 | Wilson |
| 7,115,892 | B2 | 10/2006 | Nishiyama et al. |
| 7,159,599 | B2 | 1/2007 | Verbeke et al. |
| 7,256,412 | B2 | 8/2007 | Nishiyama et al. |
| 7,262,425 | B2 | 8/2007 | Nishiyama et al. |
| 7,410,528 | B2 | 8/2008 | Rae et al. |
| 7,411,207 | B2 | 8/2008 | Nishiyama et al. |
| 7,520,918 | B2 | 4/2009 | Zoeller |
| 2003/0112437 | A1 | 6/2003 | Enomoto et al. |
| 2003/0174320 | A1 | 9/2003 | Minami et al. |
| 2004/0000186 | A1 | 1/2004 | Hagg et al. |
| 2006/0151926 | A1 | 7/2006 | Zoeller |
| 2006/0174695 | A1 | 8/2006 | Miyashita et al. |
| 2007/0022724 | A1 | 2/2007 | Gargano et al. |
| 2007/0132988 | A1 | 6/2007 | Gargano et al. |
| 2007/0238191 | A1 | 10/2007 | Gargano et al. |
| 2008/0173071 | A1 | 7/2008 | Park et al. |
| 2009/0051909 | A1 | 2/2009 | Kato |
| 2010/0201983 | A1* | 8/2010 | Hatano et al. .................. 356/337 |
| 2012/0297863 | A1 | 11/2012 | Wood et al. |

FOREIGN PATENT DOCUMENTS

| | | |
|---|---|---|
| EP | 2 103 928 A2 | 9/2009 |
| JP | 09-229662 A | 9/1997 |
| JP | 10-123067 A | 5/1998 |
| JP | 2000-193582 A | 7/2000 |
| JP | 2008-241531 A | 10/2008 |
| WO | 2004-086008 A | 7/2004 |
| WO | 2006/069006 A2 | 6/2006 |
| WO | 2007/015810 A2 | 2/2007 |
| WO | 2007/126692 A2 | 11/2007 |
| WO | 2008/091496 A2 | 7/2008 |
| WO | 2011/102949 A1 | 8/2011 |

OTHER PUBLICATIONS

International Preliminary Report on Patentability for corresponding PCT Application No. US2011/053226 filed Sep. 26, 2011; dated Jan. 21, 2013.
Second Written Opinion for corresponding PCT Application No. US2011/053226 filed Sep. 246, 2011; dated Sep. 24, 2012.
Asanuma, New Visualization and Imaging techniques for engine combustion research, Atlas Visualization, 1996, 1-43 2.
Baba et al., Analysis of transient thermal characteristic of automobile catalytic converters, Nippon Kikai Gakkai Ronbunshu B-hen, 1995, 3622-3628, 61(590), Nippon Kikai Gakkai.
Bruneaux, Liquid and vapor spray structure in high-pressure common rail diesel injection, Atomization and Sprays, IFP Rueil-Malmaison France, 2001, Abstract Only, 11, (5), Begell House, Inc. New York.
Chen et al., Visualization of immiscible displacement in a three-dimensional transparent porous medium, Experiment in Fluids, 1986, 336-338, 4(6).
Elsasser et al., Mixing phenomena of fuel sprays in intake manifolds, IClass 94, proceedings of the International Conference on Liquid Atomization and Spray System, Rouen France, Jul. 1994, 758-765, Begell House, Inc. New York.
Im et al., Visualization and measurement of automotive electrostatic rotary-bell paint spray transfer process, Journal of Fluids Engineering, Jun. 2001, 237-245, 123(2), American Society of Mechanical Engineers.
Matteson ed. et al., Filtration Principles and Practices, 1987, 626, $2^{nd}$ ed., Marcel Dekker, New York.
McDonald, Scanning High-Efficiency Air Filters for Leaks Using Particle Counting Methods, Journal of the IES, Sep.-Oct. 1993, Abstract Only (full article pp. 28-37), 36(5).
Raber, Overview from Fluid Filtration: Gas, ASTM Symposium on Gas and Liquid Filtration Philadelphia, PA, Oct. 1986, ix, 1, ASTM, Baltimore, MD.
Ruiz et al., Solid Aerosol Removal Using Ceramic Filters, Separation and Purification Technology, 2000, 221-227, 19.
Talley et al., The 2-D laser sheet visualization of a pulsed hollowed cone spray: stagnant and simulated two-stroke engine environments, Atomization and Sprays, 1991, 98-112, 1(1).
Takagishi et al., Analysis of flow field in diesel fuel sprays by particle-image velocimetry, Nippon Kikai Gakkai Ronbunshu B-hen, 1999, Abstract Only (full article in Japanese pp. 1128-1132), 65(631), Nippon Kikai Gakkai.
Tsukada et al., Three-dimensional imaging of particle clusters in dilute gas-solid suspension flow, Canadian Journal of Chemical Engineering, Apr. 1997, 466-470, 75(2), Canadian Society for Chemical Engineering.
Watanabe et al., Flow visualization and measurement of torque converter stator blades using a laser sheet lighting method and a laser Doppler velocimeter, Society of Automotive Engineers, 1997, Abstract Only (full article pp. 15-25).
Yevseyev et al., Experimental investigation of a turbulent filtration flow, International Journal of Multiphase Flow, 1991, 103-118, 17(1).
Zeman et al., Latex Particle Retention By Microfilters, Microfiltration and Ultrafiltration Principles and Applications, 1996, 182-188 and 265-266, Marcel Dekker, Inc., New York.
Rideal, Graham. Physical measurement of pores by glass bead challenge testing, Filtration Solutions (2007), 7(2), 132-137. (Coalville, United Kingdom).
Ray, Steve Recent improvements in ceramic foam filters improve metal quality; Aluminium World, 1(2), pp. 44, 46. Sovereign Publications Ltd (2001).
Jiang, Heding;et al. Chem. Reagents Res. Inst., Beijing, Peop. Rep. China. Editor(s): Sedlacek, Blahoslav; Kahovec, Jaroslav. Synth. Polym. Membr., Proc. Microsymp. Macromol., 29th (1987), Meeting Date 1986.

* cited by examiner

SYSTEM AND METHOD FOR ANALYZING PORE SIZES OF SUBSTRATES

CLAIM OF BENEFIT OF FILING DATE

The present application is a national Phase application of and claims the benefit of the PCT Application US2011/053226, filed Sep. 26, 2011 and Provisional Application 61/388,645, filed Oct. 1, 2010, the contents of which are hereby incorporated by reference in their entirety

CLAIM OF PRIORITY

This application claims priority from U.S. Provisional Application No. 61/388,645 filed Oct. 1, 2010 incorporated herein by reference in its entirety.

FIELD OF THE INVENTION

The present invention relates to system and methods useful for identifying substrates used to isolate particulate matter or to form a barrier, such as barrier films, membranes or filters having uniform or specified pore sizes and for estimating the pore sizes thereof in a non-destructive fashion.

BACKGROUND OF THE INVENTION

Substrates that are designed to isolate particulate matter from fluids, gasses, light, and solids are well known in the art. A class of such substrates is membrane systems. Typically these membrane systems utilize a barrier that is capable of separating mixtures of fluids or separating solids or particulates from a fluid. One example includes a reverse osmosis membrane designed to remove salt from brackish or salt water. Another example includes an ultrafiltration membrane which can remove higher molecular weight organic compounds from a liquid. Another class of substrates is wall flow filters. Wall flow filters are typically ceramic based and separate particulates from fluids based on size. A common design of a wall flow filter comprises a shaped ceramic article with flow passages that extend through the article in one direction. Wall flow filters have in one direction a series of walls that define flow passages generally arranged such that the walls and flow passages are disposed parallel to one another and the walls and passages extend through the shaped ceramic article. In the direction perpendicular to the walls and flow passages the wall flow filters generally demonstrate a consistent cross-sectional shape. The cross sectional shape can be any shape which is suitable for the intended use of the wall flow filter. The cross sectional shape can be circular, oval, square, rectangular, polyhedral or a shape defined by an assembly of square, rectangular or polyhedral shaped parts. In some embodiments, the wall flow filters exhibit two faces at each end having the desired cross-sectional shape and the flow passages are perpendicular to the faces of the filter and extend from one end or face to the other end or face. Often this arrangement is referred to as a honeycomb design because each end of the filter looks similar to a honeycomb. The wall flow filter may have a square or rectangular cross sectional shape. In another preferred embodiment, the wall flow filters comprise a plurality of individually formed parts that are assembled together to form a desired cross section in the direction perpendicular to the direction of the flow passages. In this last instance the cross section of the wall flow filter comprises an assembly of the cross section of the parts used to prepare the wall flow filter and can be engineered to have any desired shape. Wall flow filters often are arranged having a plurality of walls defining a plurality of flow passages. In wall flow fillers at one end every other flow passage is plugged such that the fluids cannot pass through the end of the plugged flow passage. At the other end the neighboring passages are plugged in a similar manner. The arrangement results in a structure such that each flow passage is open at one end and plugged at the opposite end. Each flow passage is surrounded by passages that are plugged at the opposite end from which it is plugged. In order to separate particulates from a fluid stream, the fluid stream is introduced through one end of the filter into the flow passages in that end. Because the other ends of the flow passages are plugged the fluid can only exit the filter through the porous walls of the flow passage and into flow passages adjacent to the flow passage into which the fluid is introduced. The flow passages into which the fluid passes are open at the opposite end from fluid introduction. Typically, a pressure differential is maintained between the flow passage into which the fluid is initially introduced and the flow passages adjacent thereto to drive the fluid through the flow passage walls. The particulate matter contained in the fluid which is of a size greater than the pores in the walls of the flow passage is retained on the wall of the flow passage into which the fluid is introduced. The fluid flowing out of the opposite end of the filter is substantially free of particulates of a size greater than the pores found in the walls of the flow passages. In an embodiment, the manufacture of the wall flow filters is adapted to produce walls with relatively uniform pores to facilitate the desired separation. The design and manufacture of ceramic wall flow filters is well known in the art and not the subject of this invention. Substrates that can be used as films or membranes which are substantially flat and the fluids to be separated or purified are contracted with one side of the film and either prevented from passing through the film or the desired fluid is passed through the film and collected on the opposite side and the undesired material is retained on the original surface of contact. In other embodiments, the substrate is arranged in another way in a device having an inlet for feeding the fluid to be separated and an exit for recovering the purified fluid. This exit may be remote from the actual separating species. Examples of structures of this type are wall flow filters, hollow fiber membranes and spiral wound membranes systems.

In the devices in which these membranes or filters are incorporated uniformity in fabrication can allow consistent end use performance thus eliminating undesired fluids or particulate matter from flowing into the recovered fluid. If the membranes or filters have pores greater than the desired pore size or of too large of a range of pore sizes undesired particulate matter can pass through the membranes or filters or the membranes or filters do not function in an efficient manner. Such problems may render them unsuitable for use. Thus it is desired to identify membranes or filters and systems containing them which due to too large pore sizes, small pore sizes, or a wide range of pore sizes cannot perform the separation as required. Methods and apparatus for identifying defects in wall flow filters are known in the art, see Kato, US 2009/0051909; Gargano et al US 2007/0022724; Gargano et al US 2007/0238191; Hijikata et al U.S. Pat. No. 5,102,434; and Zoeller, III U.S. Pat. No. 7,520,918; all incorporated herein by reference. All of these disclosed systems and methods relate to identifying gross defects in wall flow filters and require the use of highly directional light sources, lasers, wherein a very thin sheet of light is used to locate the particulate matter exiting the wall flow filters. These methods require that the thin sheet of light be located at a finite distance from the surface of the wall flow filter.

The pore sizes of wall flow filters are conventionally determined utilizing a mercury porosimetry test. This test requires removing small sections of a wall flow filter for analysis. Thus measurement of the pore size of a wall flow filter using this test destroys the wall flow filter. Miyashita US Publication 2006/0174695, page 3 paragraphs 0033 to 0035, discloses systems such as described in the above described patents and patent publications wherein the pore size of a wall filter can be estimated. This requires measurement of the size of particulates fed to the wall filter and the addition of analytical devices which analyze the size and distribution of particles exiting the wall flow filter. Examples of such analytical devices include light scattering type particle counters, centrifugal sedimentation or gravity sedimentation type particle size measuring device and specialized image processing devices capable of measuring the particle sizes and particle size distributions. Some of these methods require complex equipment or analysis of data and often a significant amount of time is required to perform the analysis.

There is still a need for systems and methods of identifying membranes, filters and systems containing the membranes or filters which contain pores of unacceptable size or unacceptable pore size distribution, which operate in a non-destructive fashion, which identify these problems in a timely manner, such as part of the manufacturing process and which do not require complex analytical measuring devices. It is further desirable that such systems provide results in a reasonably rapid manner.

SUMMARY OF THE INVENTION

The invention is a system for determining if a substrate has acceptable pore size and/or uniformity wherein the substrates are adapted to separate fluids having at least two surfaces, a first and a second surface, which are isolated from one another and wherein the substrates or devices containing the substrates which have an exit for fluids passing through the substrate, the system comprising: a) a particle generator capable of generating particles of a controlled size which is greater than the size of particles which the substrate is adapted to pass from the first surface to the second surface; b) a system for creating a pressure differential between the first and the second surface of the substrate; c) a light source spaced from the exit of the substrate or device containing the substrate adapted for illuminating particles exiting substrate or the exit of the device containing the substrate; d) a closed flow path from the particle generator to the first surface of the substrate: e) a substrate or device holder adapted for holding the substrate or device in the proper location in the system; f) one or more of i) an image capturing system and the light scattered by the particles exiting the second surface of the substrate or the exit of the device containing the substrate is captured by the image capturing system or ii) an enclosure which is opaque or which does not transmit light which encloses the space adjacent to the second surface of the substrate or exit of the device containing the substrate; wherein the light source is disposed such that light emitted from the light source contacts particles passing from the second surface of the substrate or the exit of the device containing the substrate within the enclosure. In another preferred embodiment, the system further comprises h) a computer interface wherein the comparison of the image the image of the light scattered by the particles exiting the substrate or the exit of the device containing the substrate to the one or more reference images is performed by a computer interfaced with the system. Further the invention is a method comprising: i) providing a system according to one of the embodiments described in this application; ii) placing a substrate or device containing a substrate into the substrate or device holder; iii) contacting the particles substantially the size of the pores of the substrate with the first surface of substrate wherein there is a pressure differential between the first surface of the substrate and the second surface of the substrate; iv) directing light from the light source toward the space above the second surface of the substrate or the exit of the device containing the substrate in a manner such that the particles passing through the substrate or exiting the exit of the device containing the substrate scatter light; v) monitoring the light scattered by the particles exiting the second surface of the substrate or the exit of the device containing the substrate; and vi) comparing the light scattered to one or more reference images.

In another embodiment, the present invention relates to system for analyzing the pore size of a substrate or device containing a substrate wherein the substrate is adapted to separate fluids and has at least two surfaces, a first and a second surface, which are isolated from one another and wherein the substrates or devices containing the substrates have an exit for fluids passing through the substrate, comprising: a) a particle generator capable of generating particles of a controlled size which is substantially the size of the pores of the substrate; b) a system for creating a pressure differential between the first and the second surface of the substrate; c) a light source spaced from the exit of the substrate or device containing the substrate adapted for illuminating particles exiting the exit of the substrate or device containing the substrate: d) a closed flow path from the particle generator to the first surface of the substrate; e) a substrate or device holder adapted for holding the substrate or device in the proper location in the system; and f) one or more reference images. In a preferred embodiment, the system further comprises g) an image capturing system and the light scattered by the particles exiting the second surface of the substrate or the exit of the device containing the substrate is captured by the image capturing system.

In one embodiment, the present invention relates to a method comprising: i) providing a system for analyzing the pore size of a substrate or device containing a substrate wherein the substrate is adapted to separate fluids and has at least two surfaces, a first and a second surface, which are isolated from one another and wherein the substrates or devices containing the substrates which have an exit for fluids passing through the substrate, the system comprising, a) a particle generator capable of generating particles of a controlled size which is substantially the size of the pores of the substrate; b) a system for creating a pressure differential between the first and the second surface of the substrate; c) a light source spaced from the exit of the substrate or device containing the substrate adapted for illuminating particles exiting the exit of the substrate or device containing the substrate; d) a closed flow path from the particle generator to the first surface of the substrate; and e) a substrate or device holder adapted for holding the substrate or device in the proper location in the system; ii) placing a substrate or device containing a substrate into the substrate or device holder; iii) contacting the particles substantially the size of the pores of the substrate with the first surface of substrate wherein there is a pressure differential between the first surface of the substrate and the second surface of the substrate; iv) directing light from the light source toward the space above the second surface of the substrate or the exit of the device containing the substrate in a manner such that the particles passing through the substrate or exiting the exit point of the device containing the substrate scatter light; v) monitoring the light scattered by the particles exiting the second surface of the substrate or the exit of the device containing the substrate; vi) comparing the light scattered to one or more reference images.

In another embodiment the invention comprises a quality control system for substrates adapted to separate fluids having at least two surfaces, a first and a second surface, which are isolated from one another and wherein the substrates or devices containing the substrates which have an exit for fluids passing through the substrate, the system comprising: a) a particle generator capable of generating particles of a controlled size which is greater than the size of particles which the substrate is adapted to pass from the first surface to the second surface; b) a system for creating a pressure differential between the first and the second surface of the substrate; c) a light source spaced from the exit of the substrate or device containing the substrate adapted for illuminating particles exiting substrate or the exit of the device containing the substrate; d) a closed flow path from the particle generator to the first surface of the substrate; e) a substrate or device holder adapted for holding the substrate or device in the proper location in the system; f) an enclosure which is opaque or which does not transmit light which encloses the space adjacent to the second surface of the substrate or exit of the device containing the substrate; g) a light sensor located in the enclosure adapted to sense when the intensity of the scattered light is different than a defined intensity; wherein the light source is disposed such that light emitted from the light source contacts particles passing from the second surface of the substrate or the exit of the device containing the substrate within the enclosure.

In another embodiment, the invention is a method for identifying whether the pores of a substrate are outside of a defined range where the substrate or device containing a substrate is adapted to separate fluids and has at least two surfaces, a first and a second surface, which are isolated from one another and wherein the substrates or devices containing the substrates have an exit for fluids passing through the substrate, comprising: i) providing a system according to the previous paragraph; ii) placing a substrate or device containing a substrate into the substrate or device holder; iii) contacting the particles substantially the size of the pores of the substrate with the first surface of substrate wherein there is a pressure differential between the first surface of the substrate and the second surface of the substrate; iv) directing light from the light source toward the space above the second surface of the substrate or the exit of the device containing the substrate in a manner such that the particles passing through the substrate or exiting the exit of the device containing the substrate scatter light; wherein the light sensor is set to identify when the intensity of the light scattered by the particles is outside of a defined range.

It should be appreciated that the above referenced aspects and examples are non-limiting, as others exist within the present invention, as shown and described herein. With the careful selection of reference images, the systems and methods of the invention can be utilized as a quality control system. In preferred embodiments the systems and methods can be incorporated into manufacturing plants as in line quality control methods. The methods of the invention can be used to estimate the pore size across a substrate when there is a correlation between pore size and the intensity of scattered light. The systems and methods of the invention allow the identification of substrates and systems having unacceptable pore size and spatial non-uniformity in a non-destructive fashion and without the need for complex analytical apparatus. The systems and methods of the invention provide results in a time frame such that the systems and methods can be utilized as in line quality control methods.

DETAILED DESCRIPTION

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

This application is generally related to systems and methods for analyzing the variability in pore sizes and estimating pore sizes of substrates. The systems and methods of the invention can be utilized as a free standing analytical systems and methods or incorporated into the quality control systems and methods of a production system for such substrates. The systems can be integrated into unitary systems or can be assemblies of parts and/or subassemblies. In particular the systems and methods of the invention can be utilized to identify substrates having pore sizes outside of a set range, to identify trends in pore size variation within a manufacturing system, pore size variability across a substrate and can be utilized to rapidly estimate the pore size of a substrate without destroying the substrate. The data generated by the systems and methods can be analyzed, recorded and tracked using standard process monitoring and analysis systems.

The system of the invention as described hereinbefore which further comprises one of more of the following features in any combination: one or more light sensors located in the enclosure adapted to sense the intensity of the scattered light; the sensors are one or more photodiodes, photomultipliers or cameras; the light source provides highly directional light and forms a thin sheet of light; the thin sheet of light is disposed in a plane parallel to a plane formed by the substrate or the exit of the device containing the substrate; the light source is a laser; the light sensor is attached to the enclosure on the side disposed toward the substrate or the exit of the device containing the substrate; a computer interface wherein the comparison of the image of the light scattered by the particles exiting the substrate or the exit of the device containing the substrate to the one or more reference images is performed by a computer interfaced with the system; an image capturing system wherein an image of the light scattered by the particles exiting the second surface of the substrate or the exit point of the device containing the substrate is captured by the image capturing system: the substrate is a ceramic based honeycomb filter having two faces, one for introducing a fluid containing particles and one from which a fluid exits after having passed through porous walls of the honeycomb filter; the image capturing system is disposed opposite of the second surface of the substrate or exit from the device containing the substrate; computer software adapted for image analysis; the reference images comprise images of all of the substrates analyzed in a defined time period; any other features of the system disclosed herein and the preferred embodiments of the recited features. The method of the invention as described herein before can be performed with any combination of the system features described in the previous sentence and with any one or more of the method steps and features in any combination including the preferred embodiments of each feature listed including: the reference images are taken from three or more substrates having different pore sizes and corresponding intensities of scattered light; providing a pore size map of the referenced substrates; the pore size map of the referenced substrates is created by measurement of the pores of the referenced substrates in a plurality of places in the substrate; the pore size map of the referenced substrates is created by measurement of the pores of the referenced substrates in a plurality of places in the substrate; estimating the pore size of a substrate by comparison of the light intensity of the monitored image of the substrate to the light intensities of the referenced substrates and estimating the pore size from the comparison and pore size maps of the referenced substrates; the pore size is estimated utilizing computer software adapted for image analysis; identifying substrates that exhibit pore sizes or pore size variability which is outside of a defined range, above a defined level or below a defined level based on the comparison of the light scattered by the particles to reference images; the reference images comprise images of all of the substrates analyzed in a defined time period; identifying substrates which deviate from acceptable pore sizes or pore size variability based on comparison of the captured image of scattered light of the particles to the reference images; and any other method steps or features disclosed herein.

Substrates as used herein refer to structures comprising a filtration layer. Preferably, substrate as used herein refers to a material that has inherent thickness, that is a wall, and two surfaces, a first and a second surface, wherein the surfaces are capable of being separated from another by material between the two surfaces. Capable of being separated from one another means the two surfaces can be arranged such that a fluid can be forced to pass through the wall of the substrate to transport it from the first surface to the second surface. A filtration layer refers to a material that is designed to separate components of a fluid stream or components contained in a fluid stream from the fluid stream. The filtration layer can perform the separation based on the size of the pores in the filtration layer. Typically, where a filtration layer is designed to separate materials by size, the pore size is carefully designed. The substrate can take any form which allows the first surface and the second surface to be isolated from one another in order to force fluids to pass through the substrate. Examples of such forms include wall flow filters, flat sheets, films, hollow fibers, spiral wound membrane systems and the like. During use a substrate may be exposed or may be disposed within a system. Wherein the substrate is used in a system, the system typically is designed to isolate the first surface from the second surface. Such a system generally has an inlet for feeding a fluid mixture to the first surface of the substrate and an exit for removing the portion of the fluid which passes through the wall of the substrate. In the embodiment wherein the substrate is a wall flow filter as described hereinbefore, the wall flow filter has two faces, ends, which preferably are planar in a direction perpendicular to the direction of the flow passages. The flow passages are preferably oriented perpendicular to the plane of the two faces of the wall flow filter. At one end of the wall flow filter are openings of the flow passages. The end of the flow passage opposite to the open end is plugged with a material which is capable of preventing the flow of fluid out of the flow passage. Every open passage on a face is surrounded by plugged flow passages. In the same manner, every plugged flow passage on a face is surrounded by open flow passages. At the other end, the plugged passages are open and the open passages are plugged. The result of this design is that when a fluid is introduced at the inlet end and brought into contact with the first surface of the substrate and there is a higher pressure on the first surface of the substrate than on the second surface of the substrate, the fluid passes through the walls of the substrate from the first surface to the second surface. To the extent that the fluid contains materials of a size larger than the pores, the materials are retained on the first surface of the substrate. As used herein separating components of a fluid means separating different parts of the fluid based on the size of the components through the substrate. As used herein the first surface of the substrate is the surface or the flow passages in contact with the inlet. As used herein the second surface of the substrate is the surface or the flow passages in communication with the exit. Pore size refers to the largest size of openings contained in the substrate. Typically, substrates are engineered to have a controlled largest pore size such that the substrate is capable of separating particulate matter of a certain size from a fluid. The pore size is engineered to separate particles or compounds contained in a fluid stream of a certain size. Thus it is preferred that the pore sizes of a substrate be substantially uniform. As used herein substantially uniform means that the most of the pores of a substrate are within a defined range. The determination of an acceptable range of pore sizes is impacted by the nature of the substrate the necessary tolerances dictated by the use of the substrate and the sensitivity of the image analysis techniques utilized. As used herein deviation from the defined size or range of acceptable sizes means that the pores in the tested substrate do not meet the defined pore sizes, range of pore sizes, variability in pore sizes, or any combination thereof. These parameters vary from substrate system to substrate system and are defined by the manufacturer or the user. Exit as used herein refers to an outlet for fluids which have passed through the wall of the substrate from the first surface to the second surface, which exit is used to remove the fluids passed from the vicinity of the second surface of the substrate. In the context of a wall flow filter, the substrate refers to the walls of the flow passages and the exit of the device refers to the end of the wall flow filter in communication with the flow passages in communication with the second surface of the substrate. As used herein spatial uniformity means that the pore size is reasonably uniform across the substrate.

The system of the invention contains a source of particles. The particles may comprise any particles which are substantially the same size as the designed pores of the substrate and which can scatter light when they pass from the exit of the substrate and through a layer of light. Substantially the same size as used herein means that the particles have a distribution of sizes where few particles exit the substrate when the pore size is undesirably small and the majority of the particles exit the substrate when the pore size is undesirably large. When the particle size distribution is selected as such, the scattered light intensity will be greatest when the pore size is large, all particles will pass through the substrate, and least when the pore size is small, nearly all particles will be captured by the substrate. The mechanism at which the substrate captures particles may vary with substrate type and morphology as well as with particle type and shape. As a result, the preferred particle size is determined empirically using the described selection criteria. The particles utilized need to be capable of being diffused in a fluid. Fluid as used herein is a material that flows when subjected to the pressure differential. Preferably the fluids used herein are in the liquid or gaseous state and more preferably are in the gaseous state. The particles can be solids, liquids or gases provided the particles scatter light, more preferably they are solid or liquid. In general terms, the source of particles is a particle generator which is any device or system that can form particles of the desired size having the desired properties. In one embodiment the particles are formed from a liquid material. The particulate fluid is preferably a suspension of fine drops of liquid in air that is a mist or a fog. Preferably the particulate generator in this embodiment is a device that generates a fine particle mist, such as a sprayer, nebulizer, atomizer, and the like. The liquid used to form the particles can be any liquid that can be formed into particles which scatter light. Preferable liquids which can be used include water, glycols and the like, with water being preferred. In another embodiment, the particles can be smoke, soot, incense, wheat flour and the like. Any system that generates such particles can be used as the particle generator.

Preferably, the particles are dispersed in a carrying fluid. The carrying fluid is determined according to the nature of the substrate and the materials the substrate is designed to separate. Preferably, the fluid is a gas. The particles can be dispersed in any gas that does not harm the substrate. The gas can be air, oxygen, nitrogen, carbon dioxide or an inert gas. Preferably, the gas is air. Preferably, the air is filtered to remove entrained particulate matter prior to dispersing the particles therein. In some embodiments, the system can comprise a source of gas. Any source of gas which is capable of transporting the particles and which does not harm the substrate or the system in which it is disposed may be used. The source of gas can be a pressurized tank of the desired gas, a blower, preferably with a filter for the gas or a combination thereof.

The system may further comprise a device for dispersing the particles into the carrying fluid. Any system that facilitates dispersal of the particles into the carrying fluid that facilitates contacting the particles with the substrate may be used. Such dispersal devices include a sprayer, a mixing chamber containing an impeller or air jet, a static mixer, an ultrasonic atomizer or a recirculator. In one embodiment, the dispersal device is a chamber into which the particles are introduced which further contains a blower which disperses the particles into air, and preferably further contains an impeller.

The system utilizes a device for creating a pressure differential across the wall of the substrate. The pressure differential is between the first surface of the substrate and the second surface of the substrate, in particular the pressure on the first surface is higher than the pressure on the second surface of the substrate. Any device which creates the pressure differential may be used. In one embodiment, a device which increases the pressure on the first surface of the substrate may be used. Examples of devices which increase pressure on the first surface of the substrate include gas blowers, pressurized gas tanks, a gas compressor and combinations thereof. In another embodiment, a device which reduces the pressure on the second surface of the substrate may be utilized. In a preferred embodiment, a vacuum is created on the region in contact with the second surface. Examples of means for creating a vacuum in the region in contact with the second surface of the substrate include a vacuum pump, a molecular diffusion pump, a syringe pump, or a combination thereof. The pressure differential is chosen such that the carrying fluid is driven through the wall of the substrate from the first surface to the second surface and carried away from the second surface. The particular pressure differential needed is dependent on the nature of the substrate, the nature of transport of the fluid through the substrate, the nature of the fluid and the size of the pores of the substrate. Any pressure differential which causes the carrying fluid to pass through the wall of the substrate from the first surface to the second surface may be utilized. In a preferred embodiment, the pressure differential is about 1 pascal or greater, more preferably about 4 pascals or greater, and most preferably about 6 pascals or greater. In a preferred embodiment, the pressure differential is about 100 pascals or less, more preferably about 50 pascals or less, and most preferably about 30 pascals or less.

The light source is any directional light source that can provide a relatively flat sheet of light which sheet can be disposed in a controllable manner in a plane parallel to the substrate or exit of the device containing the substrate. Preferably the light source is a laser. Preferred lasers useful include gas lasers, solid-state lasers, and semiconductor lasers. The laser light may be directed through a lens or other means of directing light so as to shape the beam into a sheet of light. There is no limit placed on the wavelength of light used so long as the light scattered by the particles can be detected by a human or the monitoring system. The light generated may be of any wavelength visible to a human or to the monitoring system. Preferably the wavelength of light is within 380 to 750 nanometers. The light may be monochromatic, of one color. The light can also be used to produce a fluorescence or phosphorescence from the particles exiting the substrate. Particles that fluoresce or phosphoresce, by coating, doping, or chemically tagging particles with a fluorescent or phosphorescent marker, can be excited and visualized or detected using light having a wavelength that will cause the particles to fluoresce or phosphoresce. It is preferable that the light source exhibit a wavelength that matches the wavelength at which the fluorescing or phosphorescing particles fluoresce or phosphoresce. In a preferred embodiment the fluorescing or phosphorescing particles are dispersible in a fluid. Preferred fluorescing or phosphorescing particles include fluorescent or phosphorescent compounds such as fluorescein, rhodamine, phycoerythrin, platinum(II)tetra-meso-fluorophenylporphine and palladium(II)tetra-meso-fluorophenylporphine and the like. The sheet of light may be located such that the location of the particles exiting the substrate or the device containing the substrate can be identified in the image generated of the light scattering of the particles. Preferably the sheet of light is disposed about 0.1 mm or greater from the substrate or device tested, more preferably about: 0.5 mm or greater and most preferably about 1 mm or greater. Preferably the sheet of light is disposed about 40 mm or less from the substrate or device tested, more preferably about 20 mm or less, even more preferably about 15 mm or less and most preferably about 5 mm or less. The sheet of light should have sufficient thickness such that the particles will visibly scatter light when they pass through the sheet of light. Preferably the sheet of light exhibits a thickness of about 0.05 mm or greater, more preferably about 0.2 mm or greater and most preferably about 1 mm or greater. Preferably the sheet of light exhibits a thickness of about 50 mm or less, more preferably about 30 mm or less and most preferably about 10 mm or less.

The system preferably comprises an interface to a computer. Any standard, interface with a computer may be utilized. Such an interface functions to allow the images captured to be stored or compared to reference images. The interface may also allow an operator to recall reference images or test images as desired or needed. The interface may also allow data derived from the images to be used in process control systems or process data collection and/or analysis systems. Such computer interfaces are well known in the art. The system of the invention may further comprise a data processing or computer system. Such system may perform any of the functions recited hereinbefore. The system of the invention may be connected by the interface to a standalone personal computer, a networked computer, a mainframe computer or a server for storing and analyzing data. Such computer systems are well known in the art. The computer system may be adapted to perform comparison of tested images to reference images. The computer system can also prepare a pore size map of the reference substrates or tested substrates. A computer with image comparison software can be used for this purpose. Examples of useful image comparison software packages include those know to the skilled artisan and include: ImageJ image analysis software (freeware available on the internet), Clemex Vision PE image analysis software, Image-Pro Plus image analysis software, and Mathematica image analysis software, (all available commercially), or the like.

In one embodiment the system of the invention may comprise an enclosure disposed about the second surface of the substrate or the exit of the device containing the substrate. The sheet of light is disposed within the enclosure and further disposed in the enclosure is a sensor adapted to sense when the intensity of light scattered by the particles exiting the substrate or the device containing the substrate is outside of a preselected range. Preferably the enclosure is opaque or does not transmit light. In one preferred embodiment the sensor senses when the light intensity is outside of a defined range or above or below a defined level that is related to the average pore size of the whole substrate. The sensor can be any sensor that is capable of sensing light intensities. Preferably the sensor is a photodiode, a photomultiplier tube, a camera, and the like. More preferably the sensor is a photomultiplier tube or a camera. The light sensitive sensors may be disposed on the surface of the enclosure or suspended from the surface of the enclosure. The surface referred to in this context is the surface of the enclosure facing the substrate or the exit of the device facing the substrate. The light source may be located in the enclosure or the enclosure may be adapted with a portal for introducing the light into the enclosure. Where a lens is utilized to shape the light, the lens can be integrated into the enclosure. The enclosure may be constructed of any material that facilitates the function of the enclosure and which does not interfere in the functioning of the system. In this embodiment an image capturing device is not required. An image capturing device may be included on the other hand so as to capture an image of a substrate device for which the sensor senses that the light intensity does not meet predefined standards.

The flow path is adapted to transport the carrier fluid containing particles from the source of particles and source of carrier fluid to the first surface of the substrate or in the inlet of a device containing the substrate, in the embodiment wherein the substrate is a wall flow filter to the inlet face of the filter. The flow path can be of any shape and manufactured from any material which facilitates introduction of the fluid containing particles to the surface of the substrate. In a preferred embodiment, the flow path creates a closed environment which can be pressurized to create a pressure differential. In one embodiment, the flow path creates a closed chamber, in another embodiment the flow path can be connected to a device for mixing the carrier fluid and the particles and collectively these parts can form a sealed chamber which is capable of being pressurized. The closed chamber can contain a pressure sensor and or regulator, an inlet for introduction of particles, an inlet for introduction of a fluid wherein the fluid may be pressurized, a blower to create pressure, or an inlet from a blower to create pressure, a gas compressor or any combination thereof. In a preferred embodiment, a seal is located between the flow path and the substrate or device containing the substrate. The seal is adapted to seal between the flow path and the substrate or the device containing the substrate and to maintain pressure of the chamber where the chamber is pressurized. Any seal that performs this function may be utilized. The seal may be an elastomeric material and in one embodiment may comprise a gas filled bladder of a flexible or elastomeric material which is capable of conforming to the substrate or device containing the substrate. The flow path and the chamber perform the additional function of isolating the first surface of the substrate from the second surface of the substrate.

The surface of the substrate or the exit of the device containing the substrate is monitored for exiting particles. The particles exiting scatter light and the scattered light is visible to the naked eye or the monitoring system. Thus the monitoring can be performed manually. The system preferably comprises an image capturing system to capture and preferably save images of the light scattered by those particles exiting from the device. Any imaging system which allows the capture of images of particles passing through the incident light may be used. The image capturing system preferably records the images in a known recording medium in a manner such that the images can be examined in order to identify the intensity of the light scattered at different areas of the substrate or the exit of the device containing the substrate, quantitatively describe the intensity of the light scattered in a number of ways such as from the grey scale intensity from a monochrome camera or from the color intensity from a color camera. The imaging device may be an analog or digital device. The imaging system can comprise an imaging device which captures a series of static or still images or it may capture a real time video image. The imaging system is preferably connected to computer system such that images cart be stored and/or further processed to determine the intensity of light scattered and quantitative differences in scattered light across the surface of the substrate or exit of the device containing the substrate. These operations can be performed by visual inspection or by computer based image processing and image analysis. In another preferred embodiment, the imaging system includes a monitor which shows the image or the image processed in a manner such that the locations of the differences in light intensity are identified. The image capturing system can be adjusted to filter out unwanted images or light wavelengths. Where the light source is a monochromatic light source the image capturing system can be adjusted to filter out all light except the monochromatic light wavelength band emitted by the light source.

The image capturing system may be located in reference to the substrate or the exit of the device containing the substrate such that an accurate image of the light scattered by the particles exiting can be observed and/or captured. Preferably the image capturing system is located opposite the substrate or the exit of the device containing the substrate. Opposite as used in this context means that the image capturing device faces the substrate or the exit of the device containing the substrate. More precisely a line projecting from the center of the lens of the image capturing system to the center of the substrate or exit of the device containing the substrate should generally be substantially perpendicular to the line projected from the center of the light source to the point in the light emitted from the light source which is above the center point of the substrate or exit of the device containing the substrate. Generally this line is parallel to the plane of the substrate surface or exit of the device containing the substrate. To provide another frame of reference, the angle between a first line projecting from the light source over the center of the substrate or the exit of the device containing the substrate and a second line projecting from the center of the lens of the image capturing device to the center of the substrate or the exit of the device containing the substrate is preferably about 165 degrees or less, more preferably about 135 degrees or less and most preferably less than about 95 degrees. Preferably the angle is about 15 degrees or greater, more preferably 45 degrees or greater and most preferably 85 degrees or greater. For a frame of reference the angles start from the line between the center of the light source and the point above the center of the of the center point of the substrate or exit of the device containing the substrate.

The system of the invention further comprises reference images of scattered light by particles exiting the substrate or exit of the device containing the substrate. The reference images function to define the appropriate standards of light intensity and/or examples of unacceptable light intensities or variations in light intensity. The reference images utilized can be in any form which facilitates the necessary comparison of tested substrates or devices containing tested substrates based on the manner in which the comparison is made. The reference images can be stored and/or displayed in any manner which facilitates the comparison. The reference images can be copies of the images stored or posted near the testing location such that an operator can manually compare with the tested image. The images can be stored in an electronic medium such as the memory of a device which allows the images to be recalled as needed. The images can be displayed manually or automatically on a screen, such as a television or computer monitor. The images can be stored in a storage media connected to a computer to facilitate recovery, sorting, identification and viewing of the reference images. The images can be generated by any method that allows their later use. Images of the light scatter of particles exiting preselected substrates or devices may be utilized. The substrates or devices may be selected based on the devices meeting acceptable standards, not meeting acceptable standards or both. Alternatively, the images may be generated by a select number or all of the substrates or devices tested in a process. A static set of standards or reference images may be used or the standards and reference images may be changed periodically or as needed. Such standards or reference images can be used to generate a map of acceptable or unacceptable light intensities and/or estimated pore sizes.

The system of the invention may optionally include a baffle which is disposed at or near the second surface of the substrate or at the exit of the system. The baffle functions to prevent light from the light source from contacting the substrate or the exit of the device containing the substrate thus scattering off of the substrate and interfering with the images of the light intensity of particles exiting the substrate or the device containing the substrate. The baffle preferably is large enough to cover the entire area of the second surface of the substrate or the exit of the device in which the substrate is located. In the embodiment where the substrate is in film or sheet form, the baffle preferably is of a sufficient size to cover the entire sheet or film. The shape in the direction of the plane parallel to the plane of the substrate or exit of the device containing the substrate is not critical as long as it covers the surface area of the substrate or exit. In a preferred embodiment, the baffles shape in the plane parallel to the plane of the substrate or exit of the device containing the substrate conforms to the shape of the substrate or the exit of the device containing the substrate. In the embodiment wherein the substrate is a wall flow filter, the baffle is of a size which is at least the same size and shape of the second face of the filter, which is the face from which the fluid exits the filter. The baffle functions to allow fluids including particles to travel away from the surface of the substrate and to prevent light from the light source from directly contacting the surface of the of the substrate or the exit of the device containing the substrate or to prevent the substrate or the exit of the device containing the substrate from scattering light in a manner which interferes with the images of the light intensity of particles exiting the substrate or the device containing the substrate. The baffle further comprises a plurality of openings adapted to allow any particles which exit the substrate of device containing the substrate to pass through the holes in the baffle. The baffle comprises a border which defines the size and shape of the baffle. Any structure which provides appropriate passage of the carrier fluid and particles there through may be used. In one embodiment the baffle may be a unitary structure with holes formed in the structure. Such unitary structure can be molded into the desired shape and can be prepared from any material capable of being formed or molded into the desired shape, such as metal, plastic and ceramics. In one embodiment the baffle can be a relatively thin wall flow filter placed upon the surface of the wall flow filter being tested. In one preferred embodiment, the wall flow filter utilized as a baffle is relatively thin in the direction perpendicular to the flow passages. In one embodiment, baffle having a plurality of interconnected parts which form a pattern wherein the baffle is of a sufficient size to cover the second surface or the fluid exit point of the substrate and the interconnected parts create openings that particles can pass through. In one embodiment, the passages in the baffle may be formed by a plurality of parts which interconnect to form a mesh or screen. The passages in the baffle or openings between the parts need to be sufficient to allow the fluid and particles passing through the substrate to flow away from the substrate or exit without substantial interference. The shape and dimensions of the passages or parts are chosen to achieve these stated objectives. The thickness in the plane parallel to the plane of the substrate or exit from device containing the substrate, for wall flow filters, the exit face, is selected to minimize the surface area covered by the structure defining the passages or the parts. In the direction perpendicular to the substrate or exit from the substrate, for wall flow filters the exit face, preferably the thickness is chosen so as to prevent the light from the light source from contacting, or scattering from in a manner which interferes with the images of the light intensity of particles exiting the substrate or the device containing the substrate, the substrate or exit of the device containing the substrate, for wall flow filters the exit face, and to be as thin as possible so that the location of any particles exiting can be identified as close as possible to the surface of the substrate or the exit. Preferably, the thickness in the direction perpendicular to the plane of the substrate or exit from device containing the substrate, for wall flow filters the exit face, is preferably about 100 mm or less, more preferably about 10 mm or less and most preferably about 0.2 mm or less. The minimum thickness is chosen such that the baffle has structural integrity and prevents light from contacting, or scattering in a manner which interferes with the images of the scattered light intensity of particles exiting the substrate or the device containing the substrate. Preferably, the thickness in the direction perpendicular to the plane of the substrate or exit from device containing the substrate, for wall flow filters the exit face, is preferably about 0.01 mm or greater and most preferably about 0.04 mm or greater. The openings which form the flow passages in the baffle are preferably of a size of about 0.05 mm or great, more preferably about 0.07 mm or greater and most preferably about 0.1 mm or greater. The openings which form the flow passages in the baffle are preferably of a size of about 5.0 mm or less, more preferably about 3 mm or less and most preferably about 0.3 mm or less. In a preferred embodiment, the baffle comprises a metallic, plastic, or cloth mesh, the flow passages are defined by interconnected wires or threads. In a preferred embodiment the baffle does not scatter light. The baffle is preferably black in color and has a flat matte finish.

The parts of the system of the invention can be separate modules which are arranged to function as described herein. Alternatively, a portion of or all of the parts can be integrated or held in place by a support structure. Such a support structure can hold and align appropriately some or all of the parts. The system of the invention and in a preferred embodiment the support structure, further comprises a holder for the substrate or the device containing the substrate. The holder along with the flow path preferably cooperates to isolate the first surface from the second surface. The holder may further comprise a known restraining device for restraining the substrate or device containing the substrate to hold it in an appropriate location. Such restraining devices are well known to a skilled artisan.

The system of the invention can be incorporated into a manufacturing system or plant. As part of the manufacturing system it is contemplated that the substrate or device can be manually inserted into the system of the invention. Alternatively, the device or substrate can be placed into the system utilizing a robot. The robot can be part of the system of the invention or can be separate and adapted to work with the system of the invention. Robotic systems which can be used with the system of the invention are well known to one skilled in the art.

In one embodiment the invention is a method comprising i) providing a system as described herein; ii) placing a substrate or device containing a substrate into the substrate or device holder; iii) contacting the particles substantially the size of the pores of the substrate with the first surface of substrate wherein there is a pressure differential between the first surface of the substrate and the second surface of the substrate; iv) directing light from the light source toward the space above the second surface of the substrate or the exit of the device containing the substrate in a manner such that the particles passing through the substrate or exiting the exit point of the device containing the substrate scatter light; v) monitoring the light scattered by the particles exiting the second surface of the substrate or the exit point of the device containing the substrate; and, vi) comparing the intensity of the light scattered to one or more reference images. This embodiment may further comprise generating and/or storing reference images. This method may further comprise estimating the pore size of a substrate by comparison of the light intensity of the monitored image of the substrate to the light intensities of the referenced substrates and estimating the pore size from the comparison and pore size maps of the referenced substrates. This method may comprise identifying substrates which deviate from acceptable pore sizes or pore size variability based on comparison of the captured image of scattered light of the substrates to the reference images.

In another embodiment the invention comprises a method for identifying whether the pores of a substrate are outside of a defined range or are too small or large where the substrate or device containing a substrate is adapted to separate fluids and has at least two surfaces, a first and a second surface, which are isolated from one another and wherein the substrates or devices containing the substrates have an exit for fluids passing through the substrate, comprising: i) providing an appropriate system of the invention; ii) placing a substrate or device containing a substrate into the substrate or device holder iii) contacting the particles substantially the size of the pores of the substrate with the first surface of substrate wherein there is a pressure differential between the first surface of the substrate and the second surface of the substrate; iv) directing light from the light source toward the space above the second surface of the substrate or the exit of the device containing the substrate in a manner such that the particles passing through the substrate or exiting the exit of the device containing the substrate scatter light; wherein the light sensor is set to identify when the intensity of the light scattered by the particles is outside of a defined range, above a defined level or below a defined level.

The first step of the methods of the invention is choosing the appropriate system of the invention for the defined purpose of the method. In a second step, the substrate or device containing the substrate is placed into the system of the invention such that the first surface of the substrate and the second surface of the substrate are isolated from one another. If there is a restraining device for the substrate or the device containing the substrate, the substrate or device are appropriately restrained. Where the system contains a seal, the seal is seated to insure isolation of the first surface of the substrate from the second surface of the substrate. If the seal is a bladder based seal, the bladder is expanded to form a seal by increasing the fluid pressure in the bladder. Particles are introduced into the system. They can be introduced into the system predispersed in a carrying fluid or they can be dispersed in the carrying fluid in the system. The particles dispersed in a carrying fluid are then passed through the flow path to the first surface of the substrate. In the embodiment wherein the substrate is disposed in a device, the particles are introduced into the inlet of the device. For a wall flow device the particles are introduced into the open flow passages on the inlet face of the device. A pressure differential is created across the wall of the substrate either by increasing the pressure on the first surface of the substrate or by decreasing the pressure on the second surface of the substrate. The carrying fluid passes through the walls of the substrate and the particles pass through the wall through the pores having a size greater than the particle size. A baffle may be disposed (placed) on or adjacent to the surface of the substrate or the exit from the device containing the substrate. Light from the light source is directed to form a sheet of light parallel to the surface of the or the face of the exit of the device containing the substrate. The sheet of light is monitored for particles passing through the substrate by examining it for the scattering of light by the particle passing through the sheet of light. The intensity of light scattered is compared to the reference images. The comparison can be performed by an operator comparing the intensity of the scattered light to the reference images. The reference images can be pictures that are located in a poster form, in a book or located in an electronic storage means and displayed on a monitor. In another embodiment an image of the scattered light is captured by an image capturing device. The captured images are then compared to the reference images. This comparison can be performed manually by an operator or automatically by a computer system. Where the comparison is performed automatically the computer can utilize image analysis software. The comparison can be performed by a quality control system or a statistical analysis system which may be incorporated in a broader quality control system of a manufacturing facility.

One step of the process is preparation of the reference images. The reference images can be prepared in any means which facilitates the objective of the system into which the reference images are incorporated, in one embodiment preselected substrates or devices containing substrates may be used to generate images from the scatter of light by particles passed through the substrate or device containing the substrate. The preselected substrates or devices may be selected to define a range of acceptable light intensities and/or to define the point or points at which the pore size of the substrate or device are above or below a defined range. The reference images may be taken from a portion or all of the substrates generated in a manufacturing run or plant. In one embodiment, the reference images are chosen based on the fact that the light intensities of the chosen images vary significantly. In a preferred embodiment the selected substrates or devices containing the substrates reflect a midpoint of the acceptable range and two outer points of the accepted range or two points just of outside of the acceptable range. In one embodiment the devices that the reference images are based on are mapped for pore size. In mapping a device for pore size a plurality of samples are taken from the referenced substrates. These samples are chosen to show the pore size in different locations of the substrate or device containing the substrate. In one preferred embodiment a sample is taken from each of four quadrants of the substrate. Then the pore size is determined according to known analytical techniques, such as mercury porosimetry. The measured pore sizes are compared to the scattered light intensity for each location from which the samples were taken. This data can be utilized to generate a correlation between measured pore size and light intensity scattered in the section tested. This correlation between intensity of light scattered and the pore size can be utilized to estimate the pore size of other substrates based on a comparison of the light intensities, this estimate is aided through the use of image analysis software run from a computer system. The reference images are preferably taken from three or more substrates having different pore sizes and corresponding intensities of scattered light. The method may further comprise providing a pore size map of the referenced substrates. The method may include creating the pore size map of the referenced substrates by measurement of the pores of the referenced substrates in a plurality of places in the substrate. The reference images may comprise images of all of the substrates analyzed in a defined time period.

In one embodiment, a method of the invention involves identifying substrates or devices containing substrates that are outside of a defined specification. In this method acceptable pore sizes are defined. Thereafter, light intensities which match acceptable and unacceptable pore sizes are identified. The light scattered for tested substrates or devices containing such substrates is monitored as described hereinbefore. The intensity of the light scattered is compared to reference images as described hereinbefore. Preferably the light scattered is monitored using an image capturing system and the images captured are compared to the reference images. In one preferred embodiment the comparison is performed by a computer system interfaced with the image capturing system. Based on this comparison substrates or devices containing substrates which exhibit light intensities that either do not match acceptable light intensities or which match unacceptable light intensities are identified. The substrates or devices containing the substrates which are identified as not meeting the defined specifications can be rejected or can be further analyzed. The method may further comprise estimating the pore size of a substrate by comparison of the light intensity of the monitored image of the substrate to the light intensities of the referenced substrates and estimating the pore size from the comparison and pore size maps of the referenced substrates. The pore size may be estimated utilizing computer software adapted for image analysis.

In another embodiment a method of the invention comprises method for determining if a substrate has acceptable pore size and/or uniformity wherein the substrates are adapted to separate fluids having at least two surfaces, a first and a second surface, which are isolated from one another and wherein the substrates or devices containing the substrates which have an exit for fluids passing through the substrate. The method involves utilizing a system of the invention comprising an enclosure as described herein and one or more sensors disposed in the enclosure. The method comprises the steps of generating particles, creating a pressure differential between the first side and the second side of the substrate, creating a sheet of light parallel to the face of the substrate or the exit from the device containing the substrate such that particles exiting therefrom scatter light from the sheet of light. The method may further comprise predetermining acceptable light intensities and unacceptable light intensities and setting the light sensors to indicate when either unacceptable or acceptable light intensities are scattered. The method can further comprise capturing an image of the scattered light. This captured image can be further analyzed to determine why the substrate or device containing the substrate was identified as not meeting the defined specification. Alternatively the captured images can be added to a reference library or used for statistical analysis of the manufacturing process.

Figure 1:
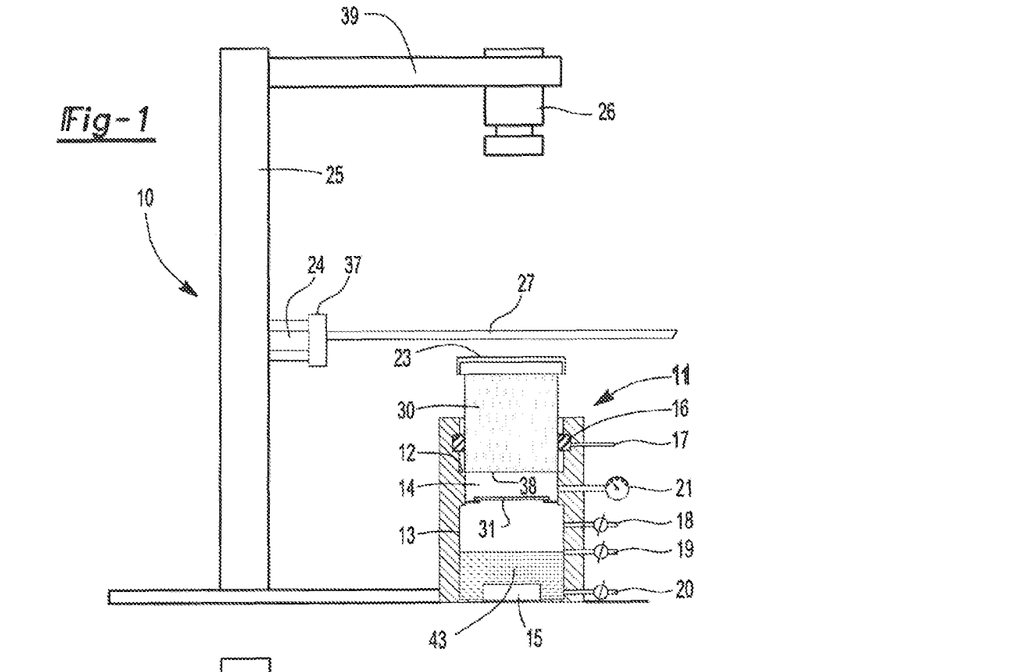
FIG. 1 illustrates one embodiment of a system of the invention.

FIG. 1 shows a system of the invention 10 containing a wall filter 30 seated in a holder 11. Shown is a holder 11 for the wall flow filter 30, wherein the filter 30 is placed on a ledge 12 which holds the filter 30 above a chamber 13 which comprises two parts, a chamber wherein the particles and the carrying fluid are mixed 38 and a flow path 14. The mixing chamber 13 and the flow path 14 are separated by a splash guard 31 to prevent water from splashing into the flow path. A humidifier or nebulizer 15 is the particle generator. The particles are generated from water in the bottom of the mixing chamber 13. A seal 16 is disposed about the outside wall of the filter 30. The seal 16 has an air inlet 17 for inflating the seal 16 about the filter 30. Shown is an air inlet 18 which introduces air as the carrying fluid. Also included is a water inlet 20 and a water outlet 19. The system has a pressure gauge 21 for monitoring the pressure in the chamber 13. An exit from the filter 23 is located at the end of the filter 30 opposite to the end 43 into which the particles are introduced. A light source (a laser) 24 is shown attached to the support structure 25. Attached to an arm 39 of the support structure 25 is an imaging assembly 26. A beam of light exits the laser 24 and is formed into a sheet of light 27 using optics 37.

In operation, a filter 30 is placed onto the ledge 12 of the holder 11. Air is introduced through the air inlet 17 to seat the seal 16 around the outside wall of the filter 30. The particle generator 15 forms particles from the water located in the bottom of the mixing chamber 38. Air is introduced through the air inlet 18 and water particles and air are mixed in the mixing chamber 38. The mixture of water particles and water are transported into the flow path 14 and then into contact with the first surfaces 43 of flow passages of the filter 30 open to the flow passage 14. A pressure differential is created by introducing pressurized air into to chamber 13 by air inlet 18. The air flows through the walls of the flow passages of the filter 30. The water particles are either retained on the first surface of the walls or pass through the pores of the wall filter 30. The particles passing through wall filter 30 flow through the flow passages in contact with the second surface of the walls out through the exit from the wall flow filter 23. The particles exiting the filter 30 scatter light generated by the light source 24. The imaging assembly 26 takes images of the scattered light from the particles. The images can be used to determine if the wall flow filter meets predefined specifications or to estimate the size of the pores of the wall flow filter 30.

Figure 2:
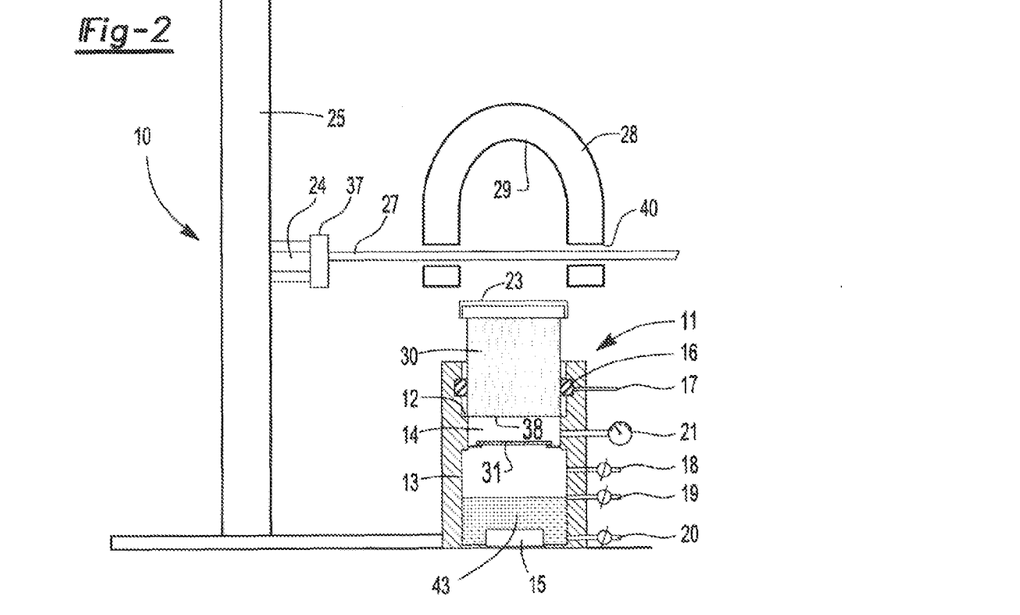
FIG. 2 illustrates a second embodiment of a system of the invention.

FIG. 2 illustrates another embodiment of a system 10 of the invention wherein an enclosure 28 is disposed about the exit from the wall flow filter 30. The sheet of light 27 is introduced through a port 40 adapted to introduce light into the enclosure 28. Disposed inside of the enclosure 28 is a sensor 29 adapted to sense when the intensity of the scattered light is of a predetermined level.

Figure 3:
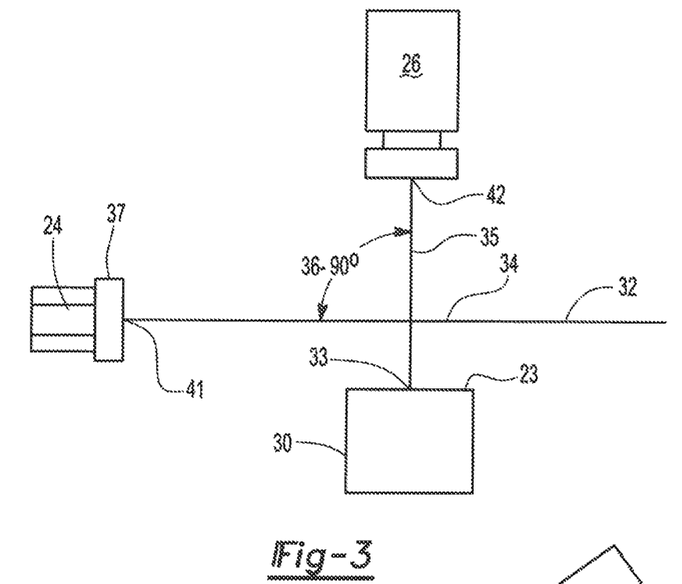
FIGS. 3 and 4 illustrates the relative angles created by the line taken from the center of the light source running through the centerpoint above exit of a substrate and the line running from the center of an image capturing system and the centerpoint of the exit of a substrate.
Figure 4:
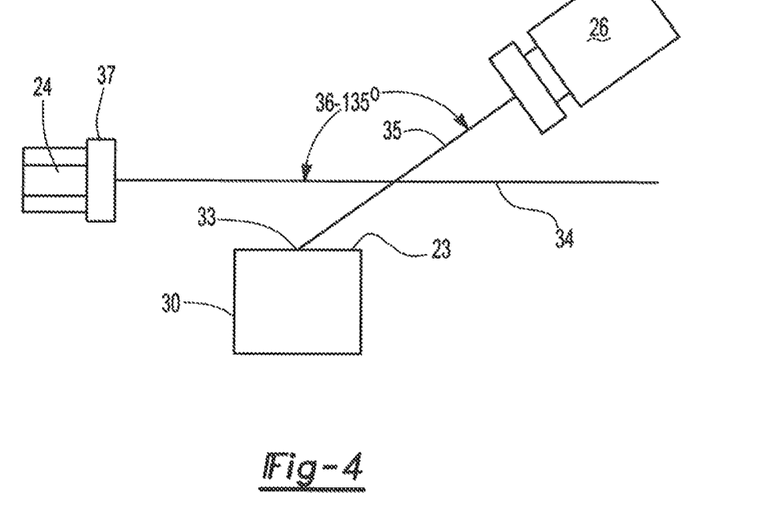

FIGS. 3 and 4 provide a frame of reference for determining the angle between the line 32 from the center 41 of the light source through a point 34 in the light sheet 27 which is above the center point 42 of the substrate 30 or exit 23 from the device containing the substrate and the line 35 from the centerpoint 42 of the image capturing device 26 and the center point 33 of the substrate 30 or exit 23 from the device containing the substrate. FIG. 3 shows a light source 24 and optics 37 adjacent to the light source 24. A first line 32 is shown proceeding from the light source 24 through optics 37 through a point 34 above the center point 33 of the exit 23 from the filter. This line 32 is parallel to the plane of the exit 23. The second line 35 runs from the center 42 of the image capturing device 26 to the centerpoint 33 of exit 23 from the filter 30. Angle A 36 is shown as 90 degrees. FIG. 4 shows a light source 24 and optics 37 adjacent to the light source 24. A first line 32 is shown proceeding from the light source 24 through optics 37 through a point 34 above the center point 33 of the exit 23 from the filter. This line 32 is parallel to the plane of the filter exit 23. The second line 35 runs from the center 41 of the image capturing device 26 to the centerpoint 33 of exit 23 of the filter 30. Angle A 36 is shown as 135 degrees. The flow of particles through a wall flow filter is illustrated in FIGS. 8 and 9 of commonly owned copending application PCT/US 2011/022822 published as WO 2011/102,949 incorporated herein by reference in its entirety.

The preferred embodiment of the present invention has been disclosed. A person of ordinary skill in the art would realize however, that certain modifications would come within the teachings of this invention. Therefore, the following claims should be studied to determine the true scope and content of the invention.

Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. Parts by weight as used herein refers to compositions containing 100 parts by weight. The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

What is claimed is:

1. A system for determining if a substrate has acceptable pore size and/or uniformity wherein the substrates are adapted to separate fluids having at least two surfaces, a first and a second surface, which are isolated from one another and wherein the substrates or devices containing the substrates which have an exit for fluids passing through the substrate, the system comprising:
   a) a particle generator capable of generating particles of a controlled size which is greater than the size of particles which the substrate is adapted to pass from the first surface to the second surface;
   b) a system for creating a pressure differential between the first and the second surface of the substrate;
   c) a light source spaced from the exit of the substrate or device containing the substrate adapted for illuminating particles exiting substrate or the exit of the device containing the substrate;
   d) a closed flow path from the particle generator to the first surface of the substrate;
   e) a substrate or device holder adapted for holding the substrate or device in the proper location in the system;
   f) a light capturing system that captures the light scattered by the particles exiting the second surface of the substrate or the exit of the device containing the substrate and said light capturing system having reference images of referenced substrates to define appropriate a standards of light intensity and/or examples of unacceptable light intensities or variations in intensities;
wherein from the light source is disposed such that light emitted from the light source contacts particles passing from the second surface of the substrate or the exit of the device containing the substrate and the references are compared to the light captured from the substrate and the substrate is accepted or rejected based thereon.

2. A system according to claim 1 wherein the reference images are selected from images of the light scatter of particles exiting preselected substrates or devices which meet acceptable standards, do not meet acceptable standards or both or the reference images may be generated by a select number or all of the substrates or devices tested in a process.

3. A system according to claim 1 wherein the light capturing system are one or more photodiodes, or photomultipliers.

4. A system according to claim 1 wherein the light source provides highly directional light and forms a thin sheet of light.

5. A system according to claim 1 wherein a baffle disposed at or near the second surface of the substrate.

6. A system according to claim 2 wherein the light source is the only light source employed in the apparatus.

7. A system according to claim 1 which further comprises a computer interface wherein the comparison of the image of the light scattered by the particles exiting the substrate or the exit of the device containing the substrate to the one or more reference images is performed by a computer interfaced with the system.

8. A method comprising:
i) providing a system according to claim 1 wherein f) comprises i) an image capturing system and the light scattered by the particles exiting the second surface of the substrate or the exit of the device containing the substrate is captured by the image capturing system and reference images to define appropriate standards of light intensity and/or examples of unacceptable light intensities or variations in intensities;
ii) placing a substrate or device containing a substrate into the substrate or device holder;
iii) contacting the particles substantially the size of the pores of the substrate with the first surface of substrate wherein there is a pressure differential between the first surface of the substrate and the second surface of the substrate;
iv) directing light from the light source toward the space above the second surface of the substrate or the exit of the device containing the substrate in a manner such that the particles passing through the substrate or exiting the exit of the device containing the substrate scatter light;
v) monitoring the light scattered by the particles exiting the second surface of the substrate or the exit of the device containing the substrate; and
vi) comparing the light scattered to one or more of the reference images.

9. A method according to claim 8 wherein the image capturing system is disposed opposite of the second surface of the substrate or exit from the device containing the substrate.

10. A method according to claim 8 wherein the reference images are taken from three or more substrates having different pore sizes and corresponding intensities of scattered light.

11. A method according to claim 8 further comprising providing a pore size map of the referenced substrates.

12. A method according to claim 11 wherein the pore size map of the referenced substrates is created by measurement of the pores of the referenced substrates in a plurality of places in the substrate.

13. A method according to claim 11 further comprising estimating the pore size of a substrate by comparison of the light intensity of the monitored image of the substrate to the light intensities of the referenced substrates and estimating the pore size from the comparison and pore size maps of the referenced substrates.

14. A method according to claim 13 wherein the pore size is estimated utilizing computer software adapted for image analysis.

15. A method according to claim 8 further comprising identifying substrates that exhibit pore sizes or pore size variability which is outside of a defined range, above a defined level or below a defined level based on the comparison of the light scattered by the particles to reference images.

16. A method according to claim 8 wherein the reference images comprise images of all of the substrates analyzed in a defined time period.

17. A method according to claim 16 further comprising identifying substrates which deviate from acceptable pore sizes or pore size variability based on comparison of the captured image of scattered light of the particles to the reference images.

18. A method according to claim 8 wherein the light source provides highly directional light and forms a thin sheet of light.

* * * * *